United States Patent [19]

Lepoutre

[11] 4,025,472
[45] May 24, 1977

[54] PROCESS FOR DRYING POLYMER-MODIFIED CELLULOSE FIBRES AND PRODUCTS PRODUCED THEREBY

[75] Inventor: Pierre Lepoutre, Pointe Claire, Canada

[73] Assignee: Pulp and Paper Research Institute of Canada, Canada

[22] Filed: June 24, 1975

[21] Appl. No.: 589,941

[30] Foreign Application Priority Data

June 26, 1974 Canada .......................... 203445/74

[52] U.S. Cl. ........................ 260/17.4 GC; 128/284; 128/285; 128/290 R; 128/296
[51] Int. Cl.² ........................ C08L 1/02; C08L 1/26
[58] Field of Search ............ 260/17.4 GC, 17.4 CL; 128/290 R, 296, 284, 285

[56] References Cited

UNITED STATES PATENTS 3,935,099  1/1976  Weaver et al. ..................... 210/43

Primary Examiner—Edward M. Woodberry
Attorney, Agent, or Firm—Millen & White

[57] ABSTRACT

An economic process is provided for effectively drying wet, highly swollen, polymer-modified, cellulosic fibres to provide fibres having enhanced properties of both water and physiological liquid retention. The essential steps of the drying process are as follows: First, the hydrolyzed fibres are thoroughly washed with water, thus rendering them to a substantially maximum swollen state. The fibres are then acidified to a low, critical pH whereby the water previously retained by the alkaline fibre is released and filtered off, thus rendering them to a substantially minimum swollen state. The product may be subjected to an optional non-shearing stirring step while in a low consistency dispersion prior to the acidification step. Further treatment with an alkali non-swelling solvent mixture renders the fibres substantially water-free in their alkaline salt form. A final wash and drying step using substantially water-free solvent and heat complete the process to yield dry, polymer-modified, cellulosic fibres having enhanced properties of both water and physiological liquid retention. New fibres can be produced having water retention values above 40g/g and aqueous salt retention values above 16 g/g.

21 Claims, 3 Drawing Figures

PROCESS FOR DRYING POLYMER-MODIFIED CELLULOSE FIBRES AND PRODUCTS PRODUCED THEREBY

BACKGROUND OF THE INVENTION

This invention relates to the preparation of novel derivatives of cellulose having improved retention characteristics not only of water but also of physiological solutions, for example, urine or blood. In one particular embodiment, it relates to the production of highly absorptive forms of cellulose derivatives obtained by graft polymerization of vinyl or acrylic monomers or derivatives thereof onto cellulosic fibres, and to the highly absorptive cellulosic derivatives so formed.

In recent years there has been a rapidly growing market for disposable absorbent products such as, for example, diapers, sanitary napkins and surgical dressings. This has focussed attention on the properties and preparation of the fibre materials used to make these products. Up to the present time, conventional wood pulps have provided a large share of the fibre required as the absorptive component. However, there have been increasing efforts recently to obtain better absorptive properties than those offered by conventional wood fibres, with a view to achieving both an improved end-product and economies in manufacture.

Polymer-modified cellulosic materials containing carboxylic acid groups or hydrolyzable functional groups are now known in the art. Examples of patented procedures include those disclosed in: Canadian Pat. Nos. 756,045 and 756,046 each issued Apr. 4, 1967 to J. W. Adams and H. W. Hoftiezer; Canadian Pat. No. 793,369 issued Aug. 27, 1968 to Tee-Pak, Inc.; U.S. Pat. No. 3,553,306 issued Jan. 5, 1971 to J. A. Church; and U.S. Pat. No. 3,194,727 issued July 15, 1965 to Tee-Pak, Inc. All the above-noted procedures are general to the in situ polymerization of an olefinically unsaturated monomer containing carboxylic groups (e.g. acrylic acid or salt) or hydrolyzable functional group, e.g. ethyl acrylate, butyl acrylate or acrylonitrile. The water absorptive properties of wood pulp modified by graft polymerization of polyacrylonitrile (known hereinafter as PAN) followed by alkaline hydrolysis of the PAN-grafted fibres and subsequent washing to pH 8 to 9 has been described in J. Appl. Pol. Sci., Vol. 17, No. 10, October 1973, p. 3143. As described therein, the product comprises modified fibres which are very swollen in water and hold the water tenaciously. Water retention values after centrifugation under 900 G. for 30 minutes of up to 30 – 40 grams water per gram fibre are obtained, the amounts being dependent on graft level.

High water and physiological solution absorbency and strong binding power are of great interest in absorbent sanitary products, but the utilization of the above-described fibres in such products has been very restricted due to the difficulty and high cost associated with the removal of the substantial amounts of water retained by the hydrolyzed fibres. Conventional thermal drying procedures were found to be slow, even at elevated temperatures because the water is tenaciously held and its diffusion out of the fibres is slow. Furthermore, drying at elevated temperatures proved costly and imparted undesirable brittle properties to the fibres. Thus, if a sheet or pad of these fibres were dried, very strong interfibre bonding developed and the pad or sheet was brittle and could not be easily disintegrated into a fluff, which is the form under which fibres are generally used in absorbent products.

One procedure suggested to prevent interfibre bonding and to obtain a dry, fluffy fibre is the freeze-drying method. However, this procedure suffers the technical and commercial disadvantage that it is slow and expensive.

Another procedure suggested to prevent interfibre bonding and to accelerate the drying is the solvent-exchange drying of the hydrolyzed fibres. However, since the cost of solvent-exchange drying is a function of the quantity of solvent utilized and thus of the quantity of water to be removed, such solvent-exchange drying procedure also suffers the technical and commercial disadvantage that it is very expensive. The quantity of water to be removed can be reduced, if the solvent-exchange drying operation is carried out on hydrolyzed, filtered but unwashed fibres, the liquid retained being 8 to 10 g/g. The solvent-exchange drying may be carried out with a solvent miscible with water, non-swelling for the polymer and in which the alkali used for hydrolysis is soluble, so that the excess alkali is removed at the same time. Methanol is a good solvent for such purposes. Such solvent-exchange dried fibres are fluffy and after being placed in water and centrifuged to 900 G will have a satisfactory water retention value and thus can be used as water absorbent material. However, when they are placed in aqueous 1% NaCl, a solution used to simulate physiological solutions such as, for example, urine or blood, such fibres will not reswell satisfactorily. Accordingly, such fibres could not be used in a sanitary pad or in a disposable diaper.

The quantity of water retained in the fibres after hydrolysis can be even further reduced by carrying out the hydrolysis in a non-swelling environment, for example, by carrying out the hydrolysis in an alcohol/water system. After hydrolysis, the liquid retained can be as low as 2–3 g/g fibre. Such fibres are then solvent-exchange dried with alcohol into a fluffy mass. But again, while the fibres will reswell fully in water, they will show very little swelling when placed in 1% NaCl solution. Accordingly, such fibres could not be used in a sanitary pad or in a disposable diaper.

As noted above, for uses such as, for example, diapers, sanitary napkins, etc., absorbency of aqueous 1% NaCl is more important than absorbency of water.

SUMMARY OF THE INVENTION

In one object of this invention, processes are provided for the preparation of novel highly absorptive cellulosic materials.

In another object of this invention, novel highly absorptive cellulosic materials are provided.

In still another object of this invention, novel highly absorptive cellulosic products are provided based on PAN.

Upon further study of the specification and appended claims, further objects and advantages of this invention will become apparent to those skilled in the art.

By a broad aspect of this invention, a process is provided for obtaining a modified cellulosic material having both enhanced water retention and enhanced physiological fluid retention by grafting an olefinically unsaturated polymerizable monomer having carboxylic acid functional groups and/or hydrolyzable functional groups onto a cellulosic fibrous material, following which the grafted product is hydrolyzed or otherwise neutralized with alkali, the improvement wherein: the product is first thoroughly washed with water rendering the product to at least 50% of its maximum swollen state; the washed product is then acidified to a pH rendering the product to substantially its minimum swollen state; following which the product is converted to the salt form under non-swelling solvent conditions; and the product is then dried.

By another broad aspect of the present invention, an improvement is provided in a process in which an olefinically unsaturated polymerizable monomer having carboxylic functional groups and/or hydrolyzable functional groups thereon is graft polymerized onto a cellulosic fibrous material by any known procedure to give a graft level preferably above 40%, following which the graft product is (i) hydrolyzed, or (ii) otherwise neutralized with alkali. The improvement involves the essential sequential steps of firstly, thoroughly washing the hydrolyzed fibres with water, to provide washed fibres in at least 50% of the "maximum swollen state", preferably at least 75%, and more preferably at least 95%, retaining as much as 30 grams of water per gram of dry fibre; secondly, acidifying the fibres to a pH of 4 or less, preferably of 3.7 or less, (but preferably not to below a pH of 2.5), at which point the fibres release the retained water; thirdly, filtering the acidified fibres, to provide fibres in the substantially "minimum swollen state" retaining only about 2 grams of water per gram of dry fibre; fourthly, treating the fibre with a substantially anhydrous alkaline solvent mixture (salt of alkali metal and solvent) to render the fibres substantially anhydrous in an alkaline salt form; and fifthly, washing with a substantially anhydrous solvent and thermally drying the fibre.

As an especially preferred embodiment of this invention, it has been unexpectedly found that a product having still further enhanced WRV and SRV properties may be obtained by a modified procedure of conducting an intermediate step of agitating a low consistency dispersion of the fibres under substantially non-shearing conditions after the water washing step but before the acidification step. By "non-shearing" is meant defibrillating the fibres under such conditions that a gel is not formed. Gentle stirring of an aqueous dispersion containing not more than 1% by weight of dry fibre is an example of such "non-shearing" conditions. By continuing the agitation for a sufficient time, it is possible to obtain final products having water retention and aqueous salt retention values which have not been known heretofore, e.g. above 40, 41, 42, 43, 44 or even 45 g/gm for water, and above 16, 17, 18, 19, 20 or 21 g/gm for aqueous salt solutions.

By the utilization of the new product having enhanced WRV and SRV properties, an improvement is provided in an absorbent pad, e.g. diapers, catamenial pads or tampons, for the absorption of physiological solutions, e.g. urine or blood, such improvement residing in the fact that the absorbent portions of such pad comprise a dry cellulosic fibrous material having been prepared by the said especially preferred embodiment of this invention.

It is to be further noted in the product produced by the broad process of the invention, i.e. without the intermediate agitation step, the graft-polymerized polymer is found within the walls of the cellulose fibre and is preferentially chemically united to the cellulose molecule, the polymer being in the form of its alkali metal salt, the fibrous material having a water retention value (WRV) of at least 15 g/g and a salt retention value (SRV) of at least 6 g/g.

It has been found that the quantity of water retained by the above-described aspects and variants of hydrolyzed or alkali-treated polymer/cellulose fibres is a function of the pH. At a pH between 6 and 9, the water retention is substantially at its maximum level. (Even at a pH of 10, however, the water retention is still sufficient to derive benefits from the invention.) There is no significant change in water retention as the pH changes within the range of 6–9. At a pH of 3.3 –3.7, the water retention is at its lowest level and is, in fact, substantially the same as that of an unmodified pulp. By the present invention, in one of its preferred aspects, it has been found to be essential that the hydrolyzed or otherwise alkali-treated fibres go through their substantially fully swollen stage, preferably in a pH range of 9 to 6 before they exist in their minimum swollen state, preferably at a pH of 3.3 – 3.7 and before they are subjected to any further treatment.

Thus, the present process is based on the discovery that (a) the hydrolyzed fibres must go through a stage of swelling, and (b) the extent of swelling of the fibres, and thus the quantity of water associated with them, is determined by the pH of the slurry, and is minimum when the pH is 2.5–4, preferably not more than 3.7 and preferably above 3.

DETAILED DISCUSSION

The process in one of its specific aspects consists in: (1) grafting polyacrylonitrile onto a fibrous cellulosic material; (2) hydrolyzing the fibres under aqueous alkaline conditions; (3) removing free alkali by thoroughly washing the filtered fibres with water after the hydrolysis to provide the fibres in at least 50% of their maximum swollen state, preferably in their substantially absolute maximum swollen state; (4) acidifying the washed fibres to a pH below 4, preferably below 3.7 at which pH the fibres are in their substantially minimum swollen state; (5) filtering the slurry as a sheet or pad; (6) running through the sheet or pad a non-swelling, alkaline, solvent solution in order to render the acid fibres substantially water-free and to convert them into their alkali salt form without causing significant reswelling; (7) washing off the residual alkali with a nonswelling solvent solution; and (8) evaporating the solvent.

The fibrous cellulosic material contemplated may be wood pulp, preferably bleached pulp or pulp of dissolving grade, hydrolyzed wood pulp (e.g. Avicell) or rayon, cotton or other carbohydrates, including carboxylic alkyl celluloses and hydroxyalkyl celluloses.

The olefinically unsaturated polymerizable monomers which have hydrolyzable functional groups contemplated for use in the process of an aspect of this invention primarily are those which have been used for this purpose in the past, the contents of the references cited in the "Background of the Invention" being pertinent. These include vinyl and acrylic monomers and derivatives thereof. The functional groups on the monomers include acrylamides, acylhalides, nitriles, esters, halides and carboxylate salts. Examples include acrylamide, acrylonitrile, methacrylonitrile, acrylic esters, methacrylic esters, vinyl acetate, acrylamide, acrylyl chloride, vinyl chloride, vinylidene chloride, vinylidene cyanide, p-chloro-styrene, maleic anhydride, maleimide, fumaramide, or combinations thereof. The olefinically unsaturated polymerizable monomers bearing carboxylic groups contemplated for use in the process of an aspect of this invention are acrylic or methacrylic acid, maleic acid, fumaric acid or their alkali salts or combinations thereof.

With respect to the grafting process used, any grafting process can theoretically be used, using chemical initiators or radiation, the sole proviso being that the polymer is strongly held within the fibre structure (preferably by covalent bonds). Otherwise during washing, or during hydrolysis of the hydrolyzable polymer (acrylonitrile, acrylic or methacrylic esters, vinyl acetate, etc.) the homopolymer will be leached out.

It is preferably, when a hydrolyzable polymer is grafted, not to use a grafting process where the graft is bonded to the backbone through a hydrolyzable group such as, for example,

since after hydrolysis, the graft would become separated.

More uniform grafting from fibre to fibre and within fibres is obtained when the cellulose fibre consistency is kept low. Consistencies as high as 8% can be used if good mixing is provided.

The reaction can be effected at any temperature from 0° C. to reflux temperatures. For additional explanation of grafting procedures, attention is again directed to said references, and in addition to the U.S. Pat. No. 3,083,118 and to Paper 38, "Cellulose Graft Copolymers", J. C. Arthur, Jr. "Addition and Condensation Polymerization Processes", Advances in Chemistry Series 91, American Chemical Society, Washington, D.C., 1969.

With respect to the hydrolysis after the graft copolymerization, it is possible to use NaOH, KOH, LiOH, $NH_4OH$, or in general, any alkali hydroxide or any other alkali base sufficiently soluble in the hydrolysis medium. The concentration of the base can vary from 0.5 to 30%, but preferably is from 1.5 to 3% to prevent undue degradation of the cellulosic backbone, resulting in a loss of soluble cellulosic material.

The temperature of the hydrolysis can range from room temperature to boiling and the time may vary from a few minutes (at boiling temperature) to several days (at room temperature).

Hydrolysis, in the case of acrylonitrile, should be carried out until there are substantially no nitrile groups left. The copolymer formed is a copolymer of acrylamide and sodium acrylate, the ratio of amide to carboxyl groups depending on the extent of the hydrolysis, and would preferably be 1.0 or less.

The acidification of the hydrolyzate or other alkali-treated polymer modified fibre is carried out in two stages. In the first stage, the hydrolyzate or other alkali-treated polymer modified fibre is thoroughly washed with water and filtered. At this state the polymer modified cellulosic product is preferably in its substantially maximum swollen state and the product is in its salt form. In the second stage, the product is acidified by admixing a strong mineral acid to obtain a pH of 4.0 or less. The concentration of the mineral acid is preferably not higher than 2 N, the important factor being that the conditions of acidity and stirring be sufficient to result in a homogeneous product. At the end of this stage, the cellulosic product is in its substantially minimum swollen state and when filtered provides deswollen fibres in carboxylic acid form.

These deswollen fibres in carboxylic acid form are converted to the alkali salt form under non-swelling alkaline solvent conditions. This may be carried out in three stages. The first stage involves reacting with an alcoholic alkali solution, e.g. alcohol/sodium hydroxide, containing 0.1 to 5% NaOH by weight and preferably 1 –2% by weight sodium hydroxide. The volume of alkaline/alcohol solution used should contain enough NaOH to convert at least half and preferably all the acid groups to their salt forms. The product is then, in a second stage, washed with substantially water-free alcohol. This removes the excess alkali and the residual water. Finally, in the third stage, the product is dried.

For a commercially feasible process, the alcohol washing solvents are recovered following each stage.

BRIEF DESCRIPTION OF THE DRAWINGS

In the accompanying drawings.

DETAILED DESCRIPTION OF THE DRAWINGS

Figure 1:
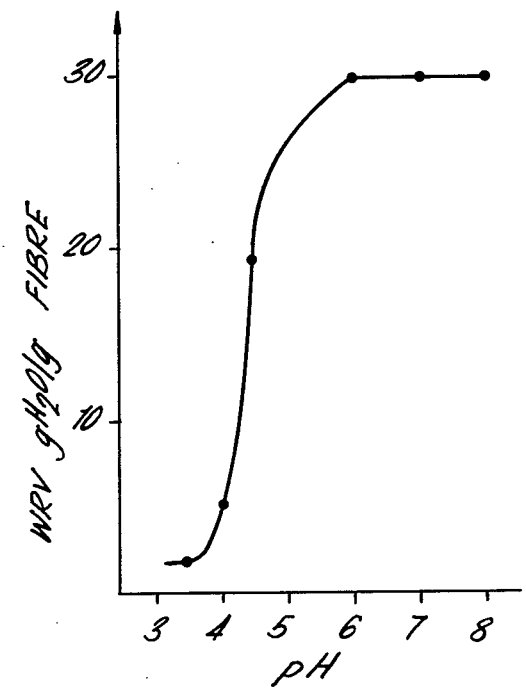
FIG. 1 is a graph showing the change in water retention value (which measures intrafibre water only) as pH is decreased, with the water retention value in gram $H_2O$/gram fibres as ordinate against pH as abscissa.

It is noted from FIG. 1 that the quantity of water retained within the fibre wall is a function of pH. From a pH of 9 down to a slightly acid pH of 6, the water retained is substantially the same, i.e. 30 g/g. Then as the pH is decreased, the amount of water retained decreases dramatically, until at pH 3.7 and lower it reaches a minimum level of 2 g/g. This is almost the level of the initial unmodified pulp.

Figure 2:
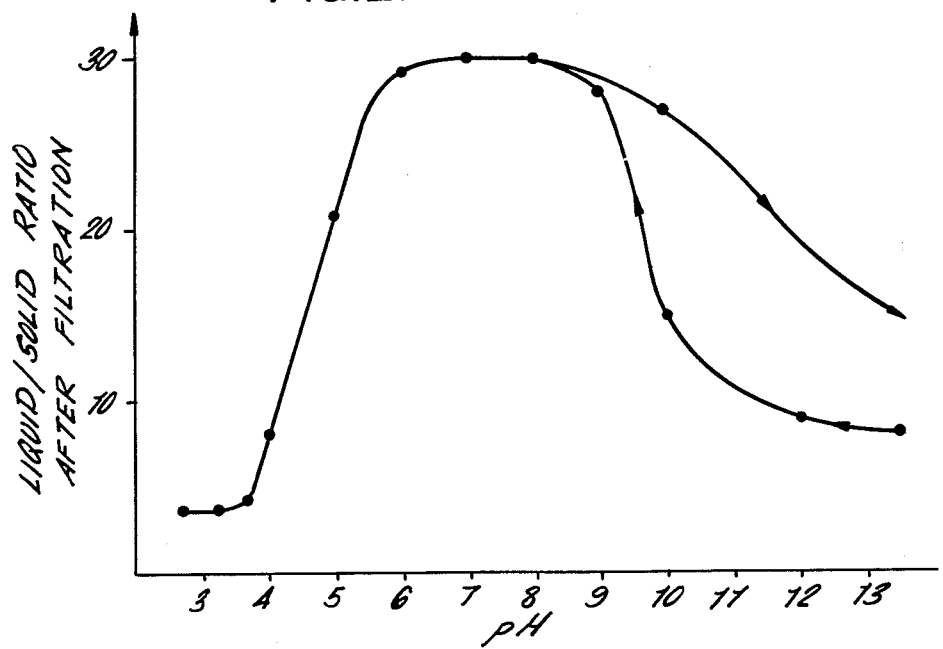
FIG. 2 is a graph showing the liquid/solid ratio after simple filtration (which includes both intrafibre water and some interfibre capillary water) versus pH with the liquid/ solid ratio after filtration as ordinate against pH as abscissa.

As seen in FIG. 2, as the pH decreases from the alkaline hydrolysis level during washing, the liquid/solid ratio increases until it has a level of 30 g/g at pH of 9–6. At this pH, the fibres have been swollen to their maximum level. Then, as also seen in FIG. 1, a decrease in pH to 4, preferably to 3.7 or lower results in fibres which retain a minimum of water, i.e. 3 –3.5% g/g. This represents a minimum swelling of the fibres.

Figure 3:
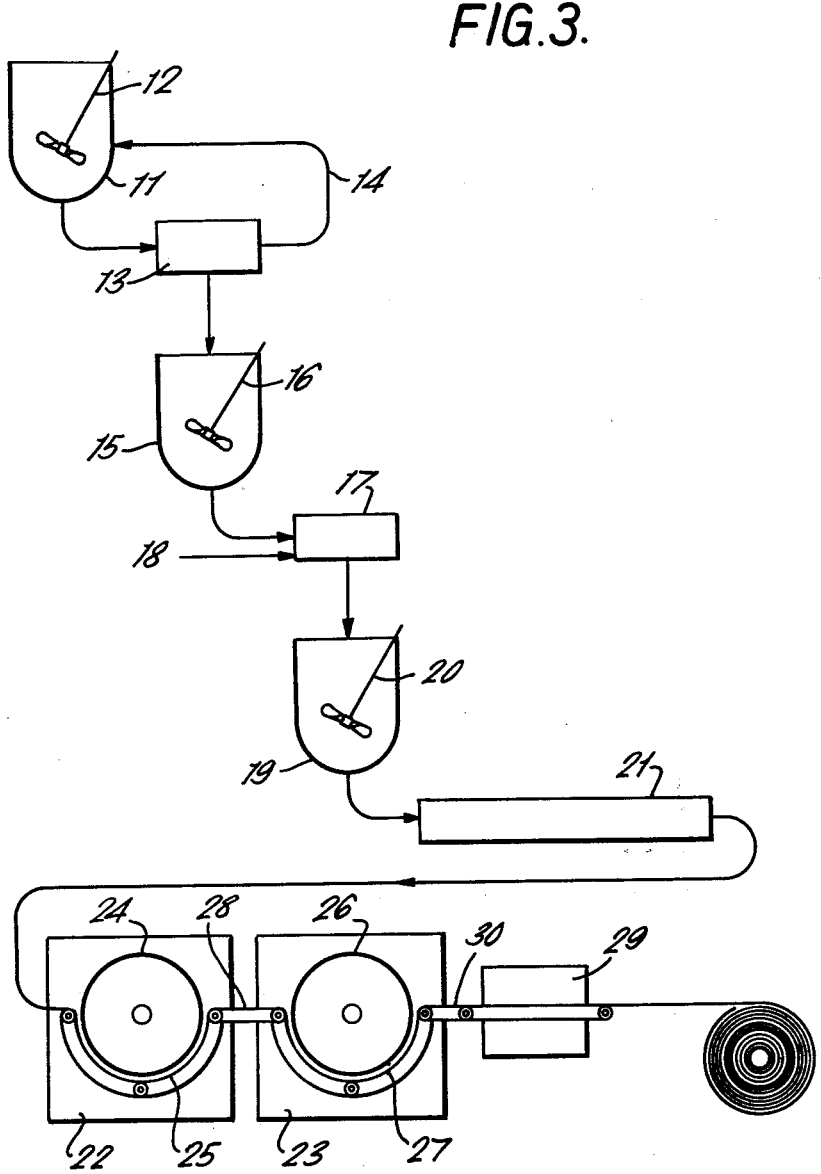
FIG. 3 is a schematic flow sheet of one manner of carrying out the process of one aspect of this invention.

As seen in FIG. 3, the grafting of polyacrylonitrile to the cellulosic materials is achieved in chamber 11 equipped with a stirrer 12. The effluent is filtered in filter 13 and the filtrate is recycled to this chamber 11 through line 14. The filtered fibres are then hydrolyzed in a hydrolysis chamber 15 equipped with a stirrer 16, using any of the above-described alkalis. The hydrolyzed or otherwise alkali-treated product is now thoroughly washed in filter vessel 17 with water introduced at 18. The fibres now in their fully swollen form are acidified in vessel 19 to a pH of 2.5 to 4 and are converted to deswollen fibres in the carboxylic acid form. This washing/ filtering/acidification procedure provides fibres in thier minimum swollen state which have passed through their maximum swollen state. The product, deswollen fibres in carboxylic acid form, is filtered or drained onto screen 21 and passed to three treating zones 22, 23 and 24 to be converted to the alkali salt form under non-swelling solvent conditions. In treating zone 22, the fibres are subjected to treatment with alcohol/ alkali (e.g. methanol/NaOH) preferably 1 to 2% by weight, to convert the fibres to the salt form under non-swelling conditions. The solvent is recovered since the fibres and solvent are passed between an arcuate continuous guide belt 25 and a vacuum drum 24. The so-treated product is passed, by conveyor 27, to zone 23, where it is treated with substantially water-free alcohol, e.g. methanol, in order to remove the excess alkali and residual water. Again the solvent is recovered since the fibres and solvent are passed between an arcuate continuous guide belt 27 and a vacuum drum 26. Finally, the material is passed through an oven, third zone 29 by conveyor 30 where it is thermally dried at a temperature sufficient to evaporate the solvent employed. The dry fibres are recovered in a fluff form. The dried fibres, such as obtained in this manner, when placed in water or 1% aqueous NaCl and centrifuged under 900 G. will reswell to their full extent and give excellent water retention and aqueous salt retention values.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE I

A never-dried Canadiam softwood bleached kraft pulp was grafted with polyacrylonitrile, using ceric ammonium nitrate as polymerization initiator. The graft level was 117%. The washed grafted fibers were then hydrolyzed as 2% slurry in 3% aqueous sodium hydroxide at boil for 30 minutes. The hydrolyzed, swollen fibres were then thoroughly washed with water and filtered. At that stage, the fibres were fully swollen. Then sulfuric acid was added until pH 3.4 was reached. Flocculation of the fibres into aggregates occurred at a pH of approximately 3.7 at which the non-ionized polyacrylic acid form predominates. The slurry of flocculated fibres at pH 3.4 was then drained freely through a coarse fitted glass Buchner funnel.

A methanol solution containing 1% by weight NaOH, tinted with phenolphthalein, was then run through the pad. The advancement of the dye front could be followed, which indicated the process of the conversion from carboxylic acid to sodium carboxylate form. The specific gravity of the eluted liquid was measured and it showed that the interfibre capillary water was eluted first, followed by methanol depleted of NaOH and diluted by water retained within the fibre, then by methanol containing 1% NaOH once all the carboxylic groups had been converted to sodium carboxylate. Pure methanol was then run through the pad to remove the excess NaOH. The solvent was then evaporated and a dry bulky, easily disintegrated pad was obtained.

After soaking some of the dried fibres in water and some in a 1% by weight aqueous NaCl for 30 minutes each, a WRV of 30 g/g and a SRV of 13.5 g/g were measured, respectively. The WRV and SRV values are essentially the same as would be obtained after solvent-exchange drying of the fully water swollen fibres after the washing step.

The above example may be repeated using other alcohols in place of methanol. Ethanol and isopropanol, for example, give equivalent results.

EXAMPLE II

The same pulp, as in Example I, was grafted with 160% PAN and hydrolyzed in 3% NaOH at boil. Following this the pulp was washed with water. One part of these fibres was acidified and converted to the sodium salt under nonswelling conditions and then dried. When WRV and SRV were measured, values of respectively, 36 and 16 were obtained.

Another part was agitated as a 1% dispersion in water, using a propeller-type stirring blade at moderate speed for 5 minutes. The fibres were then acidified and processed as described in Example I. The dried fibres, once placed in water or aqueous 1% NaCl, exhibited WRV and SRV of 40 and 19 respectively.

Another part was agitated for 20 minutes and the WRV and SRV became 45 and 21, respectively, i.e., values approximately 30% higher than that of the fibres processed without this additional agitation step.

While it is not desired to be restricted to any particular theory of operation, it is believed that polyacrylonitrile grafting is very uniform and the polymer is believed to be located between the cellulose fibre microfibrils which are the structural components of a wood fibre. After hydrolysis and washing of the excess free NaOH, due to osmotic pressure effect and configurational changes of the charged polyelectrolyte, swelling of the polymer occurs until the swelling forces are balanced by the restrictive forces due to the coherent cellulose fibre structure. The net result is a separation of the microfibrils apart from each other by the swollen polymer resulting in a dislocation of the structure which is irreversible, in the sense that, if a deswelling treatment follows, the microfibrils will not go back to their initial closely packed structure.

If this dislocation has not occurred and the fibre is contacted with aqueous NaCl, the osmotic pressure and other effects are not large enough to effect this dislocation and the fibre does not swell as much.

Applicant does not know the precise reason why this modified process provides improved WRV and SRV. However, it is believed that when the washed hydrolyzed fibres are agitated under substantially non-shearing or moderate shear conditions, a further dislocation and weakening of the fibre structure takes place which results in a more easily swellable fibre. (When used herein the term "stirring" is intended to exclude shearing stirring.) It is well known that stirring the PAN-grafted fibre product under shear conditions results in the production of a gel. The stirring action contemplated herein is "moderate" and does not result in any significant formation of gel.

While the above descriptions and procedures have mostly dealt with fibres modified by graft polymerization of monomers bearing functional groups which can be hydrolyzed to carboxylic groups or combination of carboxylic and other functional groups, such as, for example, polyacrylonitrile, it will be obvious to those skilled in the art that the same process can be applied to fibres modified by direct graft polymerization of monomers bearing carboxylic or combination of carboxylic and other groups. For instance acrylic acid, methacrylic acid or their alkali salts, or combinations of these monomers with others such as, for example, acrylamide, etc., can be directly grafted onto the wood pulp. If the acid form is used, the grafted pulp will have to be treated with an alkali to convert it to its alkali salt form, where it will be in its maximum swelling state, after which the process of acidification and conversion to the alkali salt form is carried out.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for drying modified cellulosic material having water retention properties, said cellulosic material being a graft polymerized cellulose, the grafting monomer being an alpha ethylenically unsaturated compound containing at least one functional moiety selected from the group consisting of acrylamide, acyl halide, nitrile, ester, alkenyl halide, carboxylate salt, and carboxylic acid and having been reacted with an aqueous alkali solution to hydrolyze or neutralize said functional moiety;

wherein the improvement comprises:
   a. washing resultant alkali treated cellulosic material with water to lower the pH of said material so as to swell the material to at least 50% of the maximum swollen state thereof;
   b. acidifying resultant swollen material to render the product to substantially the minimum swollen state thereof;
   c. neutralizing the resultant acidified material with alkali dissolved in a non-swelling solvent to obtain the alkali salt form of said cellulosic material; and
   d. thermally drying resultant alkali salt form of the graft-polymerized cellulosic material.

2. A process according to claim 1, wherein intermediate said steps (a) and (b), the swollen material is agitated under non-shearing, non-gel forming conditions, thereby resulting in a final product having enhanced water and physiological fluid retention.

3. The process of claim 1, wherein the pH of the swollen material is 6 – 10.

4. The process of claim 1, wherein the pH of the swollen material is 6 – 9.

5. The process of claim 1, wherein the cellulosic material in step (a) is swollen to substantially the maximum swollen state.

6. The process of claim 1, wherein the pH of the acidified material in step (b) is 2.5 – 4.

7. The process of claim 1, wherein the pH of the acidified material in step (b) is 3 – 3.7.

8. The process of claim 3, wherein the pH of the acidified material in step (b) is 2.5 – 4.

9. The process of claim 4, wherein the pH of the acidified material in step (b) is 3 – 3.7.

10. A process according to claim 9, wherein intermediate said steps (a) and (b), the swollen material is agitated under non-shearing, non-gel-forming conditions, thereby resulting in a final product having enhanced water and physiological fluid retention.

11. A process according to claim 1, wherein the monomer is acrylonitrile.

12. A process according to claim 10, wherein the monomer is acrylonitrile.

13. A process according to claim 12, wherein intermediate said steps (a) and (b), the swollen material is agitated under non-shearing, non-gel-forming conditions, thereby resulting in a final product having enhanced water and physiological fluid retention.

14. A process according to claim 1, wherein the non-swelling solvent of step (c) is a lower alkyl alcohol and the alkali is an alkali hydroxide.

15. A process according to claim 1, wherein the monomer is acrylamide, acrylonitrile, methacrylonitrile, acrylic esters, methacrylic esters, vinyl acetate, acrylyl chloride, vinyl chloride, vinylidene chloride, vinylidene cyanide, p-chloro-styrene, maleic anhydride, maleimide, fumaramide, or combinations thereof.

16. A dry cellulosic material graft polymerized with a polymer of an alpha ethylenically unsaturated monomer, said polymer having alkali carboxylate groups attached thereto, said cellulosic material exhibiting a water retention value over 40 g/g and over 16 g/g of a 1% by weight aqueous sodium chloride solution.

17. A cellulosic material according to claim 16, exhibiting retention over 41 g/g and over 17 g/g respectively.

18. A cellulosic material according to claim 16, exhibiting retention over 42 g/g and over 18 g/g respectively.

19. A cellulosic material according to claim 16, exhibiting retention over 43 g/g and over 19 g/g respectively.

20. A cellulosic material according to claim 16, exhibiting retention over 44 g/g and over 20 g/g respectively.

21. A cellulosic material according to claim 20, being a never-dried softwood bleached kraft pulp grafted with about 160% by weight of polyacrylonitrile and having been hydrolyzed in an aqueous alkali solution after the graft polymerization then subjected to the process of claim 2.

* * * * *